(12) United States Patent
Hennard et al.

(10) Patent No.: US 9,743,921 B2
(45) Date of Patent: Aug. 29, 2017

(54) SPINAL IMPLANT SYSTEM AND METHOD

(71) Applicant: Warsaw Orthopedic, Inc., Warsaw, IN (US)

(72) Inventors: Michelle M. Hennard, Memphis, TN (US); Larry T. McBride, Jr., Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 56 days.

(21) Appl. No.: 14/496,957

(22) Filed: Sep. 25, 2014

(65) Prior Publication Data

US 2016/0089129 A1 Mar. 31, 2016

(51) Int. Cl.
*A61B 17/02* (2006.01)
*A61B 17/70* (2006.01)
*A61B 17/56* (2006.01)

(52) U.S. Cl.
CPC .......... *A61B 17/02* (2013.01); *A61B 17/7002* (2013.01); *A61B 17/7032* (2013.01); *A61B 17/7037* (2013.01); *A61B 2017/0256* (2013.01); *A61B 2017/564* (2013.01)

(58) Field of Classification Search
USPC ....................................... 606/86 A
See application file for complete search history.

(56) References Cited

U.S. PATENT DOCUMENTS

| | | | | |
|---|---|---|---|---|
| 7,905,840 B2* | 3/2011 | Pimenta | ................ | A61B 1/32 600/554 |
| 8,882,811 B1* | 11/2014 | Hennard | ................ | A61B 17/56 606/279 |
| 9,060,815 B1* | 6/2015 | Gustine | ................ | A61B 17/705 |
| 2004/0133201 A1* | 7/2004 | Shluzas | ............... | A61B 17/0218 606/279 |
| 2005/0075643 A1* | 4/2005 | Schwab | ............. | A61B 17/0206 606/90 |
| 2006/0004401 A1* | 1/2006 | Abernathie | ........ | A61B 17/0206 606/198 |
| 2006/0084844 A1* | 4/2006 | Nehls | ................. | A61B 17/0206 600/227 |
| 2007/0100212 A1* | 5/2007 | Pimenta | ............... | A61B 5/0488 600/210 |
| 2008/0262318 A1* | 10/2008 | Gorek | ................ | A61B 17/0206 600/235 |
| 2013/0226239 A1* | 8/2013 | Altarac | .............. | A61B 17/7064 606/247 |
| 2014/0379032 A1* | 12/2014 | Hennard | ................ | A61B 17/56 606/279 |

OTHER PUBLICATIONS

Bashir, transcript of https://www.youtube.com/watch?v=Z5nkVaduSSg, "NuVasive XLIF—Minimally Invasive Spine Surgery" Nov. 18, 2010, transcript attached.*

* cited by examiner

*Primary Examiner* — Jan Christopher Merene

(57) ABSTRACT

A method for treating a spine includes disposing a body including vertebrae in a lateral orientation relative to a surgical fixed surface configured for supporting the body; creating an incision in tissue of the body along a substantially transverse plane of the body; spacing the tissue adjacent the incision along a sagittal plane of the body to define a surgical pathway to the vertebrae; and delivering at least one implant adjacent the vertebrae via the surgical pathway. Systems and implants are disclosed.

20 Claims, 3 Drawing Sheets

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods, connectors, plates and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior art technologies.

SUMMARY

In one embodiment, a method for treating a spine is provided. The method comprises the steps of; disposing a body including vertebrae in a lateral orientation relative to a surgical fixed surface configured for supporting the body; creating an incision in tissue of the body along a substantially transverse plane of the body; spacing the tissue adjacent the incision along a sagittal plane of the body to define a surgical pathway to the vertebrae; and delivering at least one implant adjacent the vertebrae via the surgical pathway. In some embodiments, implants and systems are disclosed.

BRIEF DESCRIPTION OF THE DRAWINGS

The present disclosure will become more readily apparent from the specific description accompanied by the following drawings, in which.

DETAILED DESCRIPTION

Figure 1:
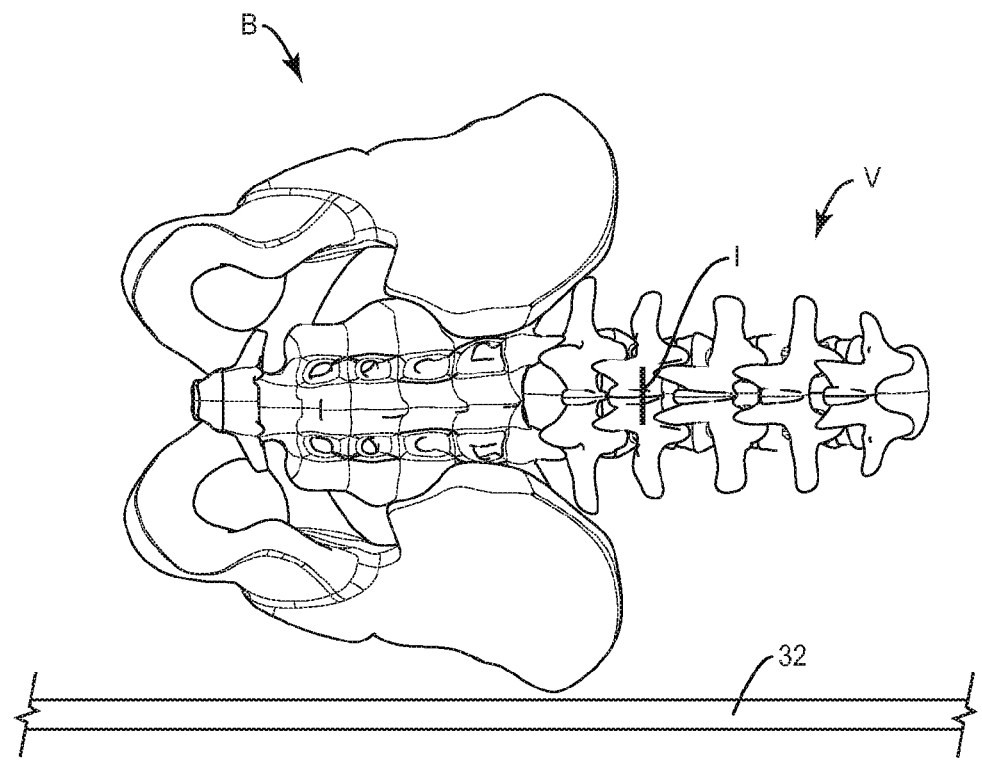
FIG. 1 is a plan view of one embodiment of a system in accordance with the principles of the present disclosure disposed with a body.
Figure 2:
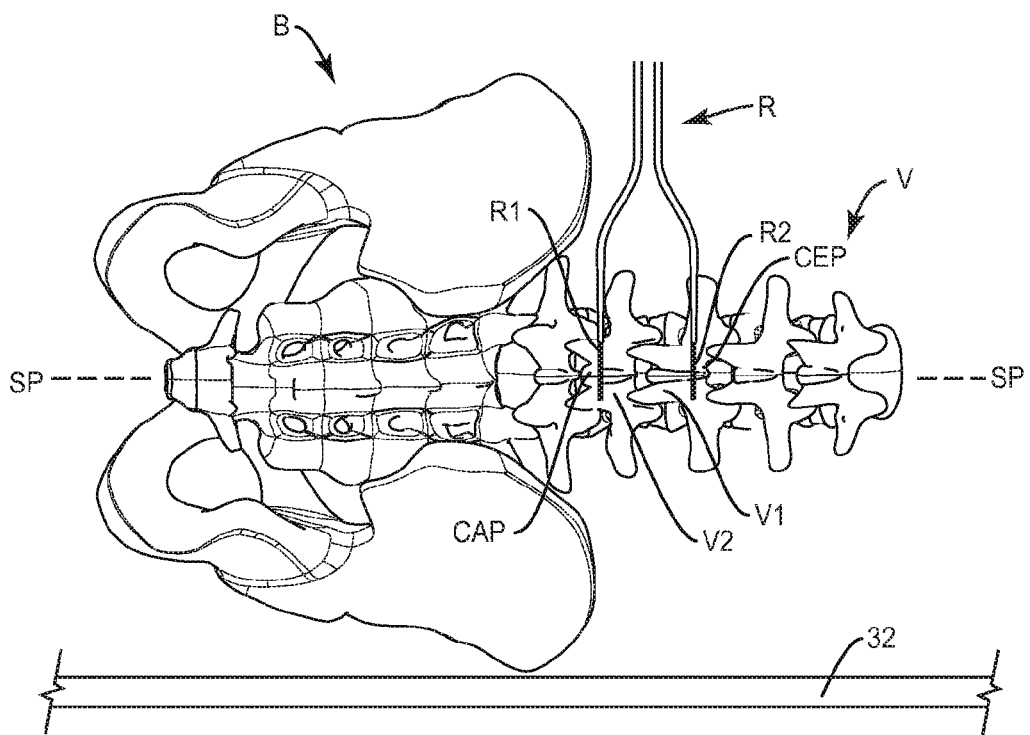
FIG. 2 is a plan view of one embodiment of a system in accordance with the principles of the present disclosure disposed with a body.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine.

In one embodiment, the system is employed with a method for implanting components of a system with a body of a patient when the body is disposed in a lateral position with a surgical fixed surface, such as, for example, a surgical table. In one embodiment, the method includes the step of making an incision in tissue of a patient perpendicular to a spinous process. In one embodiment, the method includes the step of providing a surgical instrument, such as, for example, a retractor, which is inserted into the incision. In one embodiment, the method includes the step of spacing the tissue with the retractor in a cephalad-caudal orientation. In some embodiments, this method and/or configuration avoids the effects of a force of muscle that engages the retractor adjacent a surgical site that may close the incision. In some embodiments, this method and/or configuration maintains an open incision open to deliver an implant. In some embodiments, this method and/or configuration maintains an open incision to facilitate delivery of bone screws along a cortical trajectory. In some embodiments, this method and/or configuration includes positioning the retractor with the incision, which may not require cutting adjacent muscle in a transverse orientation relative to an axis of the incision.

In one embodiment, one or all of the components of the surgical system are disposable, ped-pack, pre-packed sterile devices. One or all of the components of the surgical system may be reusable. The surgical system may be configured as a kit with multiple sized and configured components.

In one embodiment, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one embodiment, the present disclosure may be employed with other osteal and bone related applications, including those associated with diagnostics and therapeutics. In some embodiments, the disclosed surgical system and methods may be alternatively employed in a surgical treatment with a patient in a prone position, supine position, lateral position and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about"

or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 4:
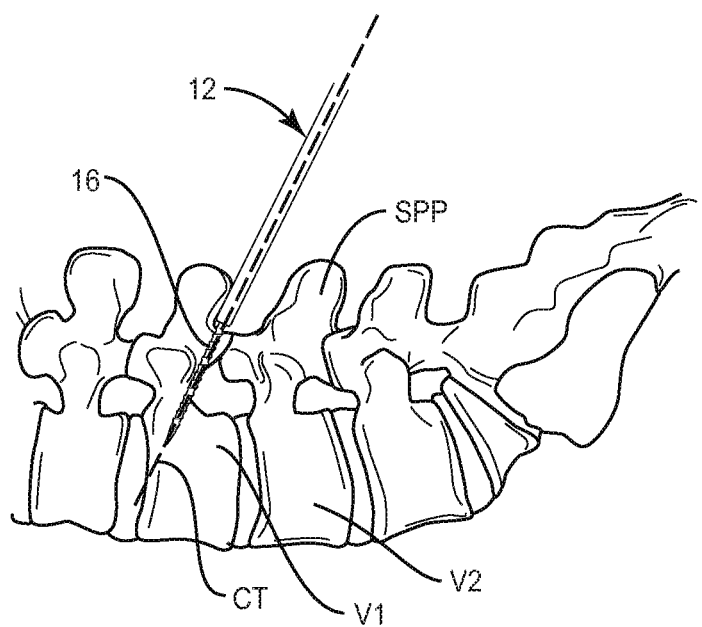
FIG. 4 is a top view of components of the system and the body shown in FIG. 1.
Figure 5:
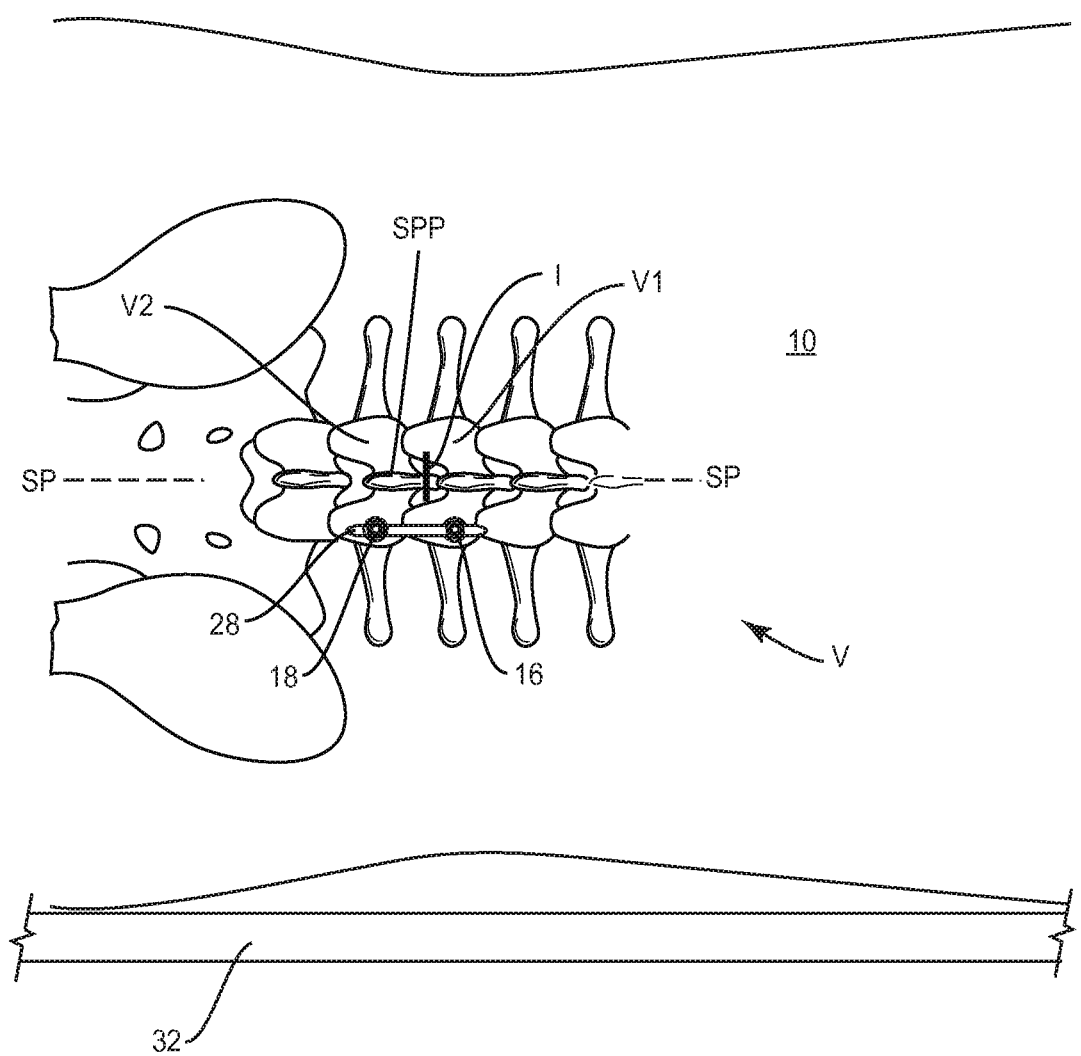
FIG. 5 is a plan view of one embodiment of a system in accordance with the principles of the present disclosure disposed with a body.

Spinal implant system 10 is employed, for example, with a minimally invasive procedure, including percutaneous techniques, and mini-open surgical techniques to deliver and introduce instrumentation and/or an implant, such as, for example, a bone fastener, at a surgical site within a body B of a patient, which includes, for example, a spine having vertebrae V, as shown in FIG. 1. Spinal implant system 10 includes an extender 12 (FIG. 4) and fasteners 16, 18 (FIG. 5). Extender 12 is configured for inserting a fastener into vertebrae V. In some embodiments, a retractor R is configured to retract tissue, such as, for example, a cephalad portion CEP and caudad portion CAP of the tissue of body B disposed adjacent a minimally invasive incision I to create an access path to a surgical site including vertebrae V. In some embodiments, spinal implant system 10 may comprise various instruments, such as, for example, inserters, reducers, spreaders, distractors, blades, clamps, forceps, elevators and drills, which may be alternately sized and dimensioned, and arranged as a kit.

In some embodiments, one or more of fasteners 16, 18 may be engaged with tissue in various orientations, such as, for example, series, parallel, offset, staggered and/or alternate vertebral levels. In some embodiments, one or more of fasteners 16, 18 may comprise multi-axial screws, sagittal angulation screws, pedicle screws, mono-axial screws, uniplanar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Each of fasteners 16, 18 comprise a first portion, such as, for example, a receiver and a second portion, such as, for example, an elongated shaft configured for penetrating tissue. The receiver includes a pair of spaced apart arms having an inner surface that defines a U-shaped passageway. One of more of the passageways are configured for disposal of a longitudinal element, such as, for example, a spinal rod 28 (FIG. 5). In some embodiments, all or only a portion of the passageway may have alternate cross section configurations, such as, for example, oval, oblong, triangular, square, polygonal, irregular, uniform, non-uniform, offset, staggered, and/or tapered. In some embodiments, the arms of the receiver may be disposed at alternate orientations, relative to the shaft, such as, for example, those alternatives described herein.

In one embodiment, each of fasteners 16, 18 have a multi axial configuration such that the receiver is rotatable to a selected angle through and within an angular range to capture a spinal rod for fixation therein. The inner surface of the receiver includes a thread form configured for engagement with a coupling member, such as, for example, a set screw. The set screw is threaded with the receiver to attach, provisionally fix and/or lock spinal rod 28 with at least one of fasteners 16, 18.

The shaft of each of fasteners 16, 18 has a cylindrical cross section configuration and includes an outer surface having an external thread form. In some embodiments, the external thread form may include a single thread turn or a plurality of discrete threads. In some embodiments, other engaging structures may be located on the shaft, such as, for example, a nail configuration, barbs, expanding elements, raised elements and/or spikes to facilitate engagement of the shaft with tissue, such as, for example, vertebrae.

In some embodiments, all or only a portion of the shaft may have alternate cross section configurations, such as, for example, oval, oblong, triangular, square, polygonal, irregular, uniform, non-uniform, offset, staggered, undulating, arcuate, variable and/or tapered. In some embodiments, the outer surface of the shaft may include one or a plurality of openings. In some embodiments, all or only a portion of the outer surface of the shaft may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of the shaft may be cannulated.

Spinal rod 28 has a cylindrical cross section configuration. In some embodiments, system 10 may include one or a plurality of spinal rods, which may be relatively disposed in a side by side, irregular, uniform, non-uniform, offset and/or staggered orientation or arrangement. In some embodiments, spinal rod 28 can have a uniform thickness/diameter. In some embodiments, spinal rod 28 may have various surface configurations, such as, for example, rough, threaded for connection with surgical instruments, arcuate, undulating, dimpled, polished and/or textured. In some embodiments, the thickness defined by spinal rod 28 may be uniformly increasing or decreasing, or have alternate diameter dimensions along its length. In some embodiments, spinal rod 28 may have various cross section configurations, such as, for example, oval, oblong, rectangular, square, polygonal, irregular, uniform, non-uniform, variable and/or tapered. In some embodiments, spinal rod 28 may have various lengths. In some embodiments, the longitudinal element may include one or a plurality of tethers.

In some embodiments, the longitudinal element may have a flexible configuration and fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of the longitudinal element includes movement in a lateral or side to side direction and prevents expanding and/or extension in an axial direction. In some embodiments, all or only a portion of the longitudinal element may have a semi-rigid, rigid or elastic configuration, and/or have elastic properties, such as the elastic properties corresponding to the material examples described above. In some embodiments, the longitudinal element may be compressible in an axial direction.

In assembly, operation and use, spinal implant system 10, similar to the systems described herein, is employed with a surgical procedure for treatment of a spinal disorder, such as those described herein, affecting a section of a spine of a patient. Spinal implant system 10 may also be employed with other surgical procedures. To treat a section of vertebrae V, which includes vertebral levels V1, V2, body B of a patient is disposed in a lateral orientation, as shown in FIGS. 1-5, relative to a surgical fixed surface, such as, for example, a surgical table 32 configured for supporting body B. In some embodiments, components, such as, implants including bone fasteners, rods, interbody devices and plates, of spinal implant system 10 are delivered and implanted with body B while maintaining body B in the lateral orientation.

With body B disposed in a selected orientation, a medical practitioner makes and/or creates a single minimally invasive incision I in tissue, which includes soft tissue and/or muscle, of body B substantially perpendicular relative to a sagittal plane SP and/or a spinous process SPP of body B to obtain access to a surgical site including vertebral levels V1, V2. In some embodiments, incision I can be disposed at alternate orientations relative to sagittal plane SP and/or spinous process SPP, such as, for example, transverse and/or angular orientations. In some embodiments, the tissue comprises cephalad portion CEP and caudad portion CAP, which includes soft tissue comprising muscle, ligaments, tendons, cartilage and/or bone, which is disposed adjacent incision I. The tissue comprising cephalad portion CEP and caudad portion CAP is manipulated in a cephalad-caudal orientation along sagittal plane SP to space the tissue adjacent incision I. In some embodiments, manipulation of incision I along sagittal plane SP in the cephalad portion CEP and caudad portion CAP avoids lifting the weight of the muscle. Manipulation of cephalad portion CEP and caudad portion CAP creates an opening and access path to a surgical site including vertebrae V.

A surgical instrument, such as, for example, a retractor R is disposed in the opening created adjacent incision I. Retractor R includes a blade R1 that engages and spaces tissue of caudad portion CAP adjacent incision I. Retractor R includes a blade R2 that engages and spaces tissue of cephalad portion CEP adjacent incision I. As such, blades R1, R2 space apart tissue of portions CAP, CEP adjacent incision I to create a surgical pathway to a surgical site including vertebrae V. In some embodiments, retractor R includes a tubular retractor, an expandable tubular retractor and/or one or a plurality of dilators, which may be concentric, to space apart tissue, as described herein. In some embodiments, retractor R spaces tissue in a cephalad direction and a caudad direction along a sagittal plane of vertebrae V. In some embodiments, the components of spinal implant system 10 are delivered percutaneously through the pathway to create an access to vertebrae V. In some embodiments, spinal implant system 10 may be used with any existing surgical method or technique including open surgery, mini-open surgery, minimally invasive surgery including percutaneous surgical implantation, whereby vertebrae V is accessed through a micro-incision, or sleeve that provides a protected passageway to the area. Once access to the surgical site is obtained, the components of spinal implant system 10 can be delivered or implanted.

In some embodiments, pilot holes are made in vertebral levels V1, V2 through the pars interarticularis. In some embodiments, the pilot holes are approximately 2 mm to 3 mm. In some embodiments, the pilot holes are made using a drill and the drill is re-oriented such that the drill is angled in the caudal to cephalad direction along sagittal plane SP. In one embodiment, the drill is oriented such that drill is inclined at the same angle as the lamina. In some embodiments, in the axial plane, the drill is moved five degrees toward spinous process SPP. In some embodiments, the drill is advanced slowly using irrigation to prevent injury to vertebrae V.

Figure 3:
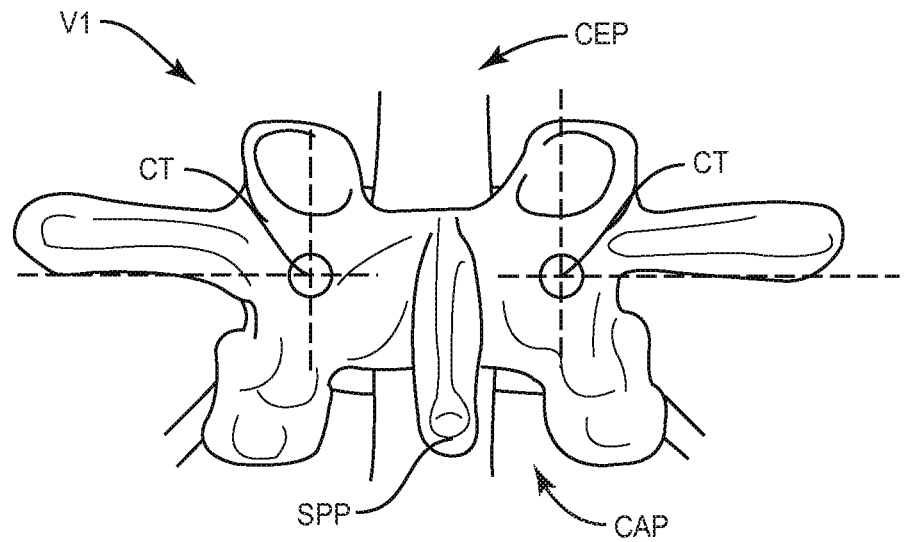
FIG. 3 is a plan view of one embodiment of trajectory for vertebrae of the body shown in FIG. 1.

With cephalad portion CEP and caudad portion CAP manipulated and/or retracted to expand the opening and/or pathway communicating with incision I, fasteners 16, 18 and spinal rod 28 are delivered through incision I. Fastener 16 is delivered along a pathway, such as, for example, a cortical trajectory CT disposed in alignment with vertebral level V1, as shown in FIGS. 3 and 4. In one embodiment, cortical trajectory CT is determined using physical landmarks and fluoroscopy simultaneously. Fastener 18 is delivered along a cortical trajectory CT, similar to trajectory CT corresponding to fastener 16, disposed in alignment with vertebral level V2. In some embodiments, one or more pilot holes are made through a pedicle of one or more selected vertebral levels along a pathway, such as, for example, a pedicle trajectory such that fasteners 16, 18 can be delivered to the surgical site along the pedicle trajectory and disposed in alignment with the vertebral level(s) to fasten fasteners 16, 18 with the pedicle of the vertebral level(s). In some embodiments, cortical trajectories CT and/or the pedicle trajectories are offset from sagittal plane SP. Extender 12 is employed to fasten one or more of fasteners 16, 18 and is disposed to resist engagement with spinous process SPP of vertebral levels V1, V2. In some embodiments, cortical trajectories CT are disposed in planes disposed in substantially parallel alignment with sagittal plane SP. In one embodiment, cortical trajectories CT are approximately 20 degrees medial-to-lateral and 30 degrees caudal-to-cephalad.

Fastener 16 is fastened with vertebral level V1 adjacent a lateral portion of vertebrae V such that fastener 16 is approximately 3 mm to 5 mm medial to the lateral edge of a pars interarticularis. Fastener 18 is similarly fastened with vertebral level V2 adjacent the lateral portion of vertebrae V. Spinal rod 28 is connected with fasteners 16, 18 by inserting spinal rod 28 through the U-shaped passageways of fasteners 16, 18 and securing spinal rod 28 with set screws, as shown in FIG. 5. In some embodiments, rods and/or fasteners are delivered to the surgical site and attached with a contra-lateral portion of vertebrae V, similar to that described herein with regard to the lateral portion of vertebrae V. In some embodiments, fasteners are delivered to the surgical site along a cortical trajectory, as described herein, and attached with vertebrae V in a bi-lateral orientation. In some embodiments, fasteners are delivered to the surgical site along a cortical trajectory, as described herein, and attached with vertebrae V in a uni-lateral orientation. In some embodiments, fasteners are delivered to the surgical site along a pedicle trajectory, as described herein, and attached with vertebrae V in a bi-lateral orientation. In some embodiments, fasteners are delivered to the surgical site along a pedicle trajectory, as described herein, and attached with vertebrae V in a uni-lateral orientation. In one embodiment, a fastener is delivered to the surgical site along a cortical trajectory, as described herein, and attached with a lateral portion of vertebral level V2, and a fastener is delivered to the surgical site along a pedicle trajectory, as described herein, and attached with a contra-lateral portion of vertebral level V1.

Upon completion of a procedure, as described herein, the surgical instruments, assemblies and non-implanted components of spinal implant system 10 are removed and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A method for treating a spine, the method comprising the steps of:
disposing a body in a lateral orientation onto a surgical fixed surface such that a sagittal plane of vertebrae of the body is disposed parallel relative to a plane defined by the surgical fixed surface;
creating an incision in tissue of the body along a substantially transverse plane of the body;
spacing the tissue adjacent the incision along a sagittal plane of the body to define a surgical pathway to the vertebrae that extends along a trajectory that intersects posterior and anterior sides of the vertebrae; and
delivering at least one implant adjacent the vertebrae via the surgical pathway.
2. A method as recited in claim 1, wherein the incision is perpendicular to a spinous process.
3. A method as recited in claim 1, wherein the tissue is spaced in a cephalad-caudal orientation.
4. A method as recited in claim 1, wherein the tissue includes muscle.

5. A method as recited in claim 1, wherein the tissue includes a cephalad portion and a caudal portion that are spaced apart.

6. A method as recited in claim 1, wherein the step of spacing includes disposing a surgical instrument within the incision to space the tissue.

7. A method as recited in claim 6, wherein the surgical instrument includes a retractor.

8. A method as recited in claim 7, wherein the retractor includes a blade that spaces a portion of the tissue in a caudal direction.

9. A method as recited in claim 7, wherein the retractor includes a blade that spaces a portion of the tissue in a cephalad direction.

10. A method as recited in claim 7, wherein the retractor includes a blade that spaces a portion of the tissue in a caudal direction and a blade that spaces a portion of the tissue in a cephalad direction.

11. A method as recited in claim 1, wherein the at least one implant includes a bone screw implanted with vertebrae along a pedicle trajectory.

12. A method as recited in claim 1, wherein the surgical pathway is oriented along a pedicle trajectory.

13. A method as recited in claim 1, wherein the at least one implant includes a bone screw implanted with vertebrae along a cortical trajectory.

14. A method as recited in claim 13, wherein the surgical pathway is oriented along a cortical trajectory.

15. A method for treating a spine, the method comprising the steps of:
    disposing a body in a lateral orientation onto a surgical fixed surface such that a sagittal plane of vertebrae of the body is disposed parallel relative to a plane defined by the surgical fixed surface, the surgical fixed surface intersecting the sagittal plane;
    creating an incision in tissue of the body along a substantially transverse plane of the body, the tissue including a first portion and a second portion disposed about the incision;
    spacing the tissue with a surgical instrument adjacent the incision along a sagittal plane such that the first portion is spaced in a caudal direction and the second portion is spaced in a cephalad direction to define a surgical pathway to the vertebrae that extends along a trajectory that intersects posterior and anterior sides of the vertebrae; and
    delivering at least one implant adjacent the vertebrae via the surgical pathway.

16. A method as recited in claim 15, wherein the incision is perpendicular to a spinous process.

17. A method as recited in claim 15, wherein the surgical instrument includes a retractor that spaces a portion of the tissue in a caudal direction and spaces a portion of the tissue in a cephalad direction.

18. A method as recited in claim 15, wherein the at least one implant includes a bone screw implanted with vertebrae along a pedicle trajectory.

19. A method as recited in claim 15, wherein the at least one implant includes a bone screw implanted with vertebrae along a cortical trajectory.

20. A method for treating a spine, the method comprising the steps of:
    disposing a body in a lateral orientation onto a surgical fixed surface such that a sagittal plane of vertebrae of the body is disposed parallel relative to a plane defined by the surgical fixed surface, the surgical fixed surface being positioned directly below the vertebrae;
    creating an incision in tissue of the body along a substantially transverse plane of the body, the tissue including a first portion and a second portion disposed about the incision; inserting a retractor with the incision;
    spacing the tissue adjacent the incision along a sagittal plane such that the first blade of the retractor spaces the first portion in a caudal direction and a second blade spaces the second portion in a cephalad direction to define a surgical pathway to the vertebrae that extends along a trajectory that intersects opposite posterior and anterior sides of the vertebrae; and
    delivering at least one bone screw along a cortical trajectory via the surgical pathway to adjacent the vertebrae.

\* \* \* \* \*

UNITED STATES PATENT AND TRADEMARK OFFICE
CERTIFICATE OF CORRECTION

| | | |
|---|---|---|
| PATENT NO. | : 9,743,921 B2 | Page 1 of 1 |
| APPLICATION NO. | : 14/496957 | |
| DATED | : August 29, 2017 | |
| INVENTOR(S) | : Hennard et al. | |

It is certified that error appears in the above-identified patent and that said Letters Patent is hereby corrected as shown below:

In Column 1, Line 3, delete "HELD" and insert -- FIELD --, therefor.

In Column 1, Line 36, delete "steps of;" and insert -- steps of: --, therefor.

In Column 2, Line 28, delete "ped-pack," and insert -- peel-pack, --, therefor.

In Column 5, Line 3, delete "friction fillings," and insert -- friction fittings, --, therefor.

Signed and Sealed this
Twentieth Day of March, 2018

Andrei Iancu
*Director of the United States Patent and Trademark Office*